| United States Patent [19]
Maul

[11] Patent Number: 4,776,986
[45] Date of Patent: Oct. 11, 1988

[54] SYNTHESIS OF HIGH PURITY 5-CHLOROISOPHTHALOYL CHLORIDE

[75] Inventor: James J. Maul, Grand Island, N.Y.

[73] Assignee: Occidental Chemical Corporation, Niagara Falls, N.Y.

[21] Appl. No.: 171,041

[22] Filed: Mar. 21, 1988

Related U.S. Application Data

[63] Continuation-in-part of Ser. No. 858,468, Apr. 30, 1986, abandoned.

[51] Int. Cl.$^4$ ............................................. C07C 51/00
[52] U.S. Cl. ................................................. 260/544 D
[58] Field of Search ..................................... 260/544 D

[56] References Cited

U.S. PATENT DOCUMENTS 3,869,510  3/1975  Gelfand et al. ................. 260/544 D

FOREIGN PATENT DOCUMENTS 57-193434  11/1983  Japan .

Primary Examiner—Howard T. Mars
Attorney, Agent, or Firm—James F. Tao; William G. Gosz

[57] ABSTRACT

A process for the preparation of high purity 5-chloroisophthaloyl chloride comprises reacting isophthaloyl chloride with liquid chlorine in the presence of a Lewis acid catalyst at a temperature of about 55° Celsius to 80° Celsius under autogenous pressure.

3 Claims, No Drawings

SYNTHESIS OF HIGH PURITY 5-CHLOROISOPHTHALOYL CHLORIDE

REFERENCE TO RELATED APPLICATION

This application is a continuation-in-part of U.S. application Ser. No. 858,468, filed April 30, 1986.

BACKGROUND OF THE INVENTION

This invention relates to an improved process for the preparation of 5-chloroisophthaloyl chloride. The product is useful as a chemical intermediate in the preparation of various products, especially agricultural chemicals, such as herbicides and the like.

U.S. Pat. No. 3,869,510 to Gelfand discloses a process for the preparation of 5-chloroisophthaloyl chloride by reaction of isophthaloyl chloride with chlorine gas in the presence of molybdenum pentachloride catalyst at a temperature of about 227° C. The 5-chloroisophthaloyl chloride product is shown to be useful in the further synthesis of 3,5-dichlorobenzoyl chloride which in turn is disclosed as a useful intermediate in the further preparation of various biologically active compounds.

U.S. Pat. No. 3,821,310 to Brunetti et al discloses the use of 5-chloroisophthaloyl chloride as an intermediate in the synthesis of 1,3-bis-(2'-hydroxy-4'-methoxy-benzoyl)-5-chlorobenzene, a product useful as a light stabilizer in polymeric materials.

Although 5-chloroisophthaloyl chloride has been known to be a useful intermediate for a number of years, the processes for its production have been found to present difficulties, especially with respect to the purity of the product. In particular, prior art processes have been found to result in the simultaneous formation of undesired isomers and over-chlorinated products, most especially the undesired isomer 4-chloroisophthaloyl chloride, and over-chlorinated products including for example, dichloroisophthaloyl chlorides. The production of isomers and over-chlorinated products results in the necessity of additional separation steps, and disposal of undesired products with a resultant economic disadvantage. The 4-chloroisophthaloyl chloride, having a boiling point close to that of 5-chloroisophthaloyl chloride, is particularly troublesome to separate.

It is an object of this invention to provide an improved process for the preparation of 5-chloroisophthaloyl chloride having improved selectivity, specifically with the enhancement of production of 5chloroisophthaloyl chloride in preference to 4-chloroisophthaloyl chloride at relatively low temperatures and with minimal overchlorination. It is a further object of this invention to provide a process whereby 5-chloroisophthaloyl chloride may be prepared at an expeditious rate while realizing the desired selectivity.

SUMMARY OF THE INVENTION

It has now been found that 5-chlorosiophthaloyl chloride may be prepared in excellent yields with minimal formation of undesired isomers and over-chlorinated side products by a process comprising; reacting isophthaloyl chloride with liquid chlorine in the presence of a Lewis acid catalyst at a temperature of about 50° to about 100° Celsius, and preferably about 55° to about 80° Celsius under autogenous conditions. The amount of chlorine supplied to the reaction mixture should be sufficient to establish a stoichiometric excess, that is, a mole ratio of chlorine:isophthaloyl chloride of greater than 1:1 and most preferably in the range of about 3:1 to about 6:1. There is no critical upper limit. However, ratios in excess of 10:1 of liquid chlorine:isophthaloyl chloride, normally provide no practical advantage. The autogenous pressure resulting from temperatures in the 50°–100° C. range will normally be in the range of about 200 to about 400 psig.

The process of this invention is carried out in the presence of a Lewis acid catalyst such as aluminum chloride, ferric chloride or the like. The preferred catalyst, based on effectiveness, availability and economic considerations is ferric chloride. The amount of catalyst employed may vary considerably, for example, from 0.1 percent or less to 5.0 percent or more, based on the weight of isophthaloyl chloride reactant. Typically the catalyst is employed in an amount of about 0.2 percent to about 2.0 percent by weight, based on the weight of isophthaloyl chloride reactant.

The following specific examples are provided to further illustrate this invention in the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A mixture of 100.4 parts of isophthaloyl chloride and 1.5 parts of ferric chloride was charged to a pressure reactor. Chlorine (107 parts) was added and the reactor was heated to 75° C. and maintained thereat for six hours. During that reaction time the reactor pressure ranged from 240 to 330 psig. The reaction product was analyzed by gas chromatographic techniques and was found to contain, in mole percent, 25% isophthaloyl chloride, 70.8% 5-chloroisophthaloyl chloride, 0.49% 4-chloroisophthaloyl chloride and 2.5% dichloroisophthaloyl chloride. The analysis is consistent with a pseudo first order rate constant of $k^* = 0.25$ hour$^{-1}$.

EXAMPLE 2

A mixture of 103 parts of isophthaloyl chloride and 4.5 parts of ferric chloride was charged to a pressure reactor. Chlorine (114 parts) was added and the reactor was heated and maintained at about 60° C. for a period of about 21 hours. During that reaction time, the reactor pressure ranged from about 200 to about 300 psig. The reaction product was analyzed by gas chromatographic techniques and found to contain, in mole percent, 11.1% isophthaloyl chloride, 84.1% 5chloroisophthaloyl chloride, 0.17% 4-chloroisophthaloyl chloride, and 4.2% dichloroisophthaloyl chloride. The analysis is consistent with a pseudo first order rate constant of $k^* = 0.105$ hours$^{-1}$.

For purposes of comparison, isophthaloyl chloride was reacted with chlorine under other conditions, with the results as set forth in the following examples.

EXAMPLE 3

A mixture of 500 parts of isophthaloyl chloride and 5 parts of ferric chloride catalyst was heated and maintained at about 180° C. at atmospheric pressure while chlorine gas was bubbled in over a period of about 11.3 hours. Analysis of the reaction product, by gas chromatographic techniques, indicated, in mole percent, 19.0% isophthaloyl chloride, 74.7% 5-chloroisophthaloyl chloride, 2.3% 4-chloroisophthaloyl chloride, and 3.7% dichloroisophthaloyl chloride. The analysis is consistent with a pseudo first order rate constant of $k^* = 0.37$ hours$^{-1}$.

EXAMPLE 4

(A) A mixture of one hundred parts of isophthaloyl chloride and 1.0 parts of ferric chloride was heated to 95° C. and maintained at that temperature for 2.3 hours. Chlorine gas was introduced into the reaction mixture at the rate of 14 grams per hour. A sample of the reaction mixture was analyzed by gas chromatography and found to contain 1.0% 5-chloroisophthaloyl chloride and 99% isophthaloyl chloride starting material. The analysis is consistent with a pseudo first order rate constant of $k^* = 0.006$ hours$^{-1}$ for consumption of isophthaloyl chloride.

(B) An additional 0.5 parts of ferric chloride was added to the reaction mixture and the temperature (95° C.) was maintained for an additional 4.5 hours. At the end of that period, a sample of the reaction mixture was analyzed by gas chromatography and found to contain, in mole percent, 91.5% isophthaloyl chloride, 8.15% 5-chloroisophthaloyl chloride, and 0.19% 4-chloroisophthaloyl chloride. The analysis is consistent with a pseudo first order rate constant of $k^* = 0.017$ hours$^{-1}$.

(C) An additional 2.0 parts of ferric chloride was added and the mixture was maintained at 95° C. for an additional 17.75 hours. At the end of that period, the reaction product was analyzed by gas chromatography and found to contain, in mole percent, 12.3% isophthaloyl chloride, 84.8% 5-chloroisophthaloyl chloride, 0.71% 4-chloroisophthaloyl chloride, and 2.8% dichloroisophthaloyl chloride. The analysis is consistent with a pseudo first order rate constant of $k^* = 0.124$ hours$^{-1}$.

The advantages of the present invention are further illustrated by the data from the preceding examples as set forth in the following table.

TABLE 1

| Example | Type of Reaction | Temperature/°C. | Yield/Mole % 5-chloroisophthaloyl chloride | Isomer Ratio** 5-ClIPC/4-ClIPC | Pseudo-First Order Rate Constant $k^*$ (× 100)hours$^{-1}$ |
|---|---|---|---|---|---|
| 1 | Autoclave | 75 | 70.8 | 144 | 25. |
| 2 | Autoclave | 60 | 84.1 | 495 | 10.5 |
| 3 | Atmospheric | 180 | 74.7 | 32 | 37. |
| 4 (A) | Atmospheric | 95 | 1.0 | — | 0.6 |
| 4 (B) | Atmospheric | 95 | 8.15 | 43 | 1.7 |
| 4 (C) | Atmospheric | 95 | 84.8 | 119 | 12.4 |

*Calculated as $k = [\ln A_o/A]/T$
A° + A are the initial and final mole fraction of isophthaloyl chloride
**5-ClIPC = 5-chloroisophthaloyl chloride
4-ClIPC = 4-chloroisophthaloyl chloride From the table it will be seen that reaction conditions of low temperature and autogenous pressure result in unexpectedly high yields and purity, effluent utilization of chlorine, and high rate of reaction.

What is claimed is:

1. A process for the preparation of 5-chloroisophthaloyl chloride which comprises reacting a mixture of isophthaloyl chloride and stoichiometric excess of liquid chlorine at a temperature of about 55° to about 80° Celsius under autogenous pressure, in the presence of about 0.1 to about 5.0 percent by weight of ferric chloride catalyst, based on the weight of isophthaloyl chloride reactant.

2. A process according to claim 1 wherein the amount of ferric chloride catalyst is about 0.2 to about 2.0 percent by weight, based on the weight of isophthaloyl chloride.

3. A process according to claim 1 which is carried out under autogenous pressure of about 200 psig. to 400 psig.

* * * * *